(12) United States Patent
Taylor et al.

(10) Patent No.: US 8,184,297 B2
(45) Date of Patent: May 22, 2012

(54) GAS MIXTURE MEASUREMENT SYSTEM AND METHODS THEREFOR

(75) Inventors: Robert Warren Taylor, Ponte Vedra Beach, FL (US); Peter Martin Maly, Lake Forest, CA (US); Brian Robert Phelan, Lees Summit, MO (US)

(73) Assignee: General Electric Company, Schenectady, NY (US)

( * ) Notice: Subject to any disclaimer, the term of this patent is extended or adjusted under 35 U.S.C. 154(b) by 328 days.

(21) Appl. No.: 12/640,797

(22) Filed: Dec. 17, 2009

(65) Prior Publication Data
US 2011/0149288 A1 Jun. 23, 2011

(51) Int. Cl.
*G01N 21/00* (2006.01)

(52) U.S. Cl. ........................................................ 356/437

(58) Field of Classification Search .................. None
See application file for complete search history.

(56) References Cited

U.S. PATENT DOCUMENTS

| | | |
|---|---|---|
| 5,173,749 A | 12/1992 | Tell et al. |
| 5,330,621 A | 7/1994 | Visuri et al. |
| 6,042,365 A | 3/2000 | Chen |
| 6,064,488 A | 5/2000 | Brand et al. |
| 7,022,992 B2 | 4/2006 | Grant et al. |
| 7,053,425 B2 | 5/2006 | Sandvik et al. |
| 7,075,653 B1 | 7/2006 | Rutherford |
| 7,231,078 B2 | 6/2007 | Wintrich et al. |
| 2006/0203248 A1 | 9/2006 | Reichardt et al. |
| 2006/0262311 A1* | 11/2006 | Muta et al. .................... 356/437 |
| 2010/0028819 A1 | 2/2010 | Knittel et al. |

FOREIGN PATENT DOCUMENTS

| | | |
|---|---|---|
| EP | 0708322 A1 | 4/1996 |
| EP | 1787103 A2 | 5/2007 |
| GB | 1475909 A | 6/1977 |
| JP | 2004219379 A | 8/2004 |
| JP | 2008116263 A | 5/2008 |
| WO | 2006022550 A2 | 3/2006 |

OTHER PUBLICATIONS

The GB Search Report issued in connection with corresponding GB Application No. GB 1020653.0 on Mar. 10, 2011.

* cited by examiner

*Primary Examiner* — Tu Nguyen
(74) *Attorney, Agent, or Firm* — Ernest G. Cusick; Hoffman Warnick LLC

(57) ABSTRACT

A system including at least one laser device extending a beam through an in-situ non-restrictive flow path of the gas mixture; and a measurer coupled to each laser device for obtaining a plurality of dynamic measurements over time of at least one species in the gas mixture.

20 Claims, 3 Drawing Sheets

GAS MIXTURE MEASUREMENT SYSTEM AND METHODS THEREFOR

BACKGROUND OF THE INVENTION

The subject matter disclosed herein relates to solutions for measuring gas mixtures. Specifically, the subject matter disclosed herein relates to in-situ measurements of species in a non-restrictive flow path of a gas mixture.

Gas mixtures are produced under various circumstances such as combustion, chemical reaction, and evaporation. The source of a gas mixture may include but is not limited to: turbines, engines, furnaces, kilns, pulverizers, piles of solid materials such as coal, enclosed material storage systems such as bins or silos, pools of liquid materials such as water treatment facilities. In any of these circumstances, it may be useful to know: (1) the concentration of one or more species in a gas mixture at any given point of time; and (2) the trend of concentrations of one or more species in a gas mixture over a period of time.

Measuring concentration of species in a gas mixture may provide information about explosive or health hazard conditions. Gas concentrations move from the source of the gas mixture via the environment, a pipe, duct or other flow paths. Obtaining several concentrations at the same point in time on a cross-section of a flow path may reveal, for example, inefficiencies in an engine or furnace. Examining trends of concentration of species in a gas mixture may provide an early warning to the development of certain conditions instead of waiting for the concentration to reach a specific level.

Extractive techniques for sampling gas mixtures extract a sample of the gas mixture for analysis using a chamber. After chambering the sample of gas mixture, a chemical analysis or an optical device analysis is applied to obtain measurements of species in the chambered sample of the gas mixture. Analysis using extractive methods delays obtaining the results of the analysis and may provide results that are not representative of the total gas volume.

BRIEF DESCRIPTION OF THE INVENTION

A first aspect of the disclosure provides a system, comprising: at least one laser device extending a beam through an in-situ non-restrictive flow path of the gas mixture; and a measurer coupled to each laser device for obtaining a plurality of dynamic measurements over time of at least one species in the gas mixture.

A second aspect of the disclosure provides a method, comprising: extending a beam with at least one laser device through an in-situ non-restrictive flow path of a gas mixture; and measuring a plurality of dynamic measurements over time of at least one species in the gas mixture.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide solutions for in-situ measurements of species in a non-restrictive flow path of a gas mixture.

Figure 1:
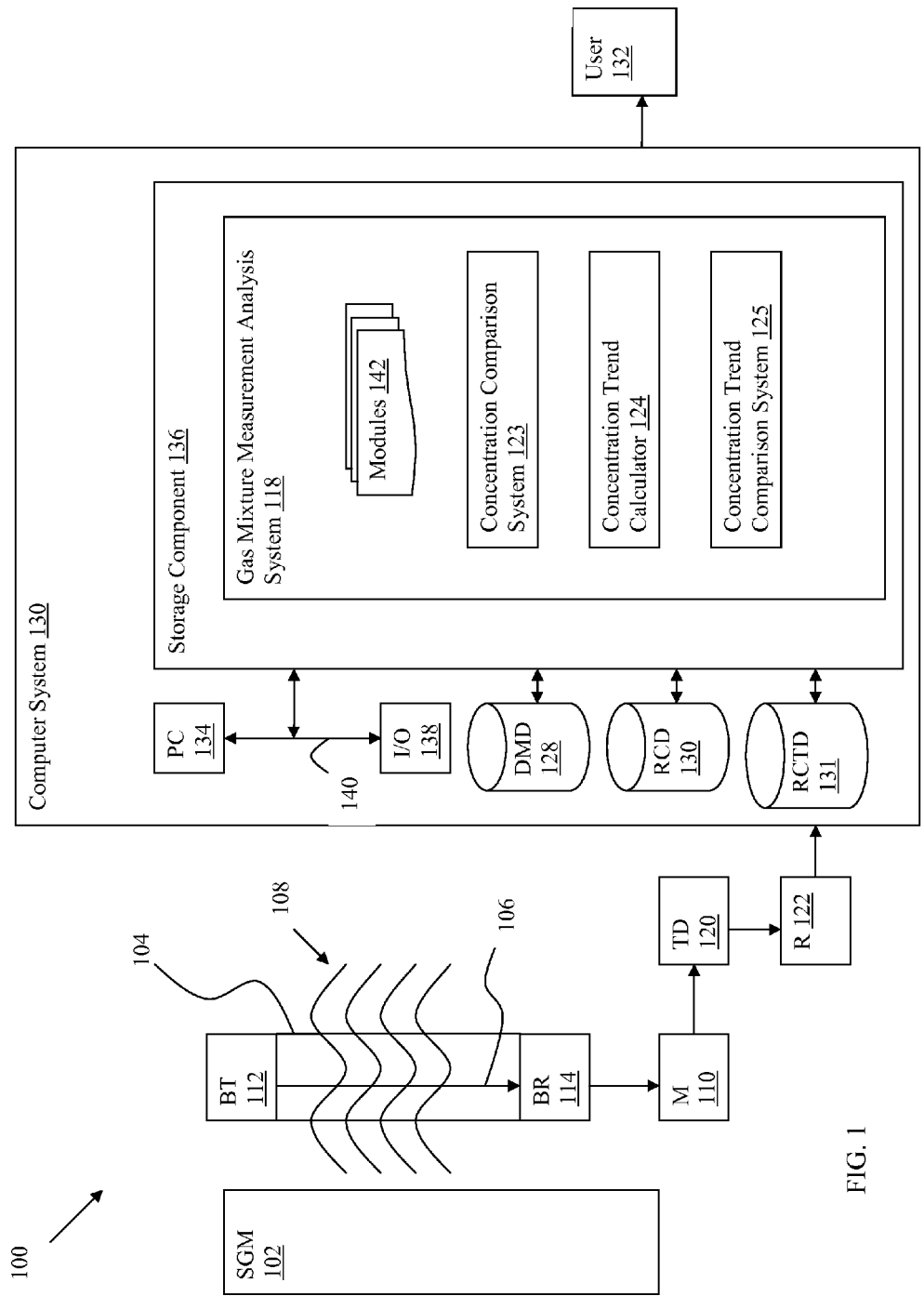
FIG. 1 shows a block diagram of one embodiment of the invention.

FIG. 1 shows an embodiment of a gas mixture measurement device 100. Gas mixture measurement device 100 includes at least one laser device 104 extending a beam 106 through an in-situ non-restrictive flow path of a gas mixture 108; and a measurer (M) 110 coupled to each laser device 104 for obtaining a plurality of dynamic measurements over time of at least one species in gas mixture 108.

FIG. 1 includes a computer system 130 that can perform the method described herein for measurements of species in in-situ non-restrictive flow path of a gas mixture 108. In particular the technical effect is, computer system 130 is shown including a gas mixture measurement analysis system 118, which makes computer system 130 operable to receive and analyze dynamic measurements by performing a process described herein.

Gas mixture 108 may be created by a source of gas mixture (SGM) 102. Source of gas mixture 102 may include any device or physical entity that generates gas mixture 108 through any physical, chemical or combustible means. For example, an engine or furnace may release gas mixture 108 as a by-product of combustion. As another example, a pile of coal may release gas mixture 108 due to chemical reactions in the pile. As another example, a pool of liquid may evaporate releasing gas mixture 108. A species includes molecules of a chemical that may be a part of gas mixture 108.

The in-situ non non-restrictive flow path of gas mixture 108 may include gas mixture 108 as it emerges or flows from source of gas mixture 102 without additional diverging or chambering from source of gas mixture 102 for the purpose of taking a gas mix measurement.

Each laser device 104 includes a beam transmitter (BT) 112 and a beam receiver (BR) 114. Each laser device 104 may be calibrated to identify a species when beam 106 is extended through gas mixture 108. Calibration to identify species is based upon the amount of beam attenuation when beam 106 strikes a species. The species may include but not be limited to CO, $CH_4$, NO, $NO_2$ and $CO_2$. Laser device 104 may include, for example, a quantum cascade laser (QCL), a tunable diode laser (TDL), a vertical cavity surface emitting laser (VCSEL), and an interband cascade laser (ICL).

Each laser device 104 is placed or mounted within the in-situ non-restrictive flow of gas mixture 108. Beam transmitter 112 and beam receiver 114 are oriented in order for beam 106 to extend through gas mixture 108. Measurer 110 obtains dynamic measurement of at least one species in gas mixture 108. Each dynamic measurement may include a concentration and a time of measurement.

Figure 2:
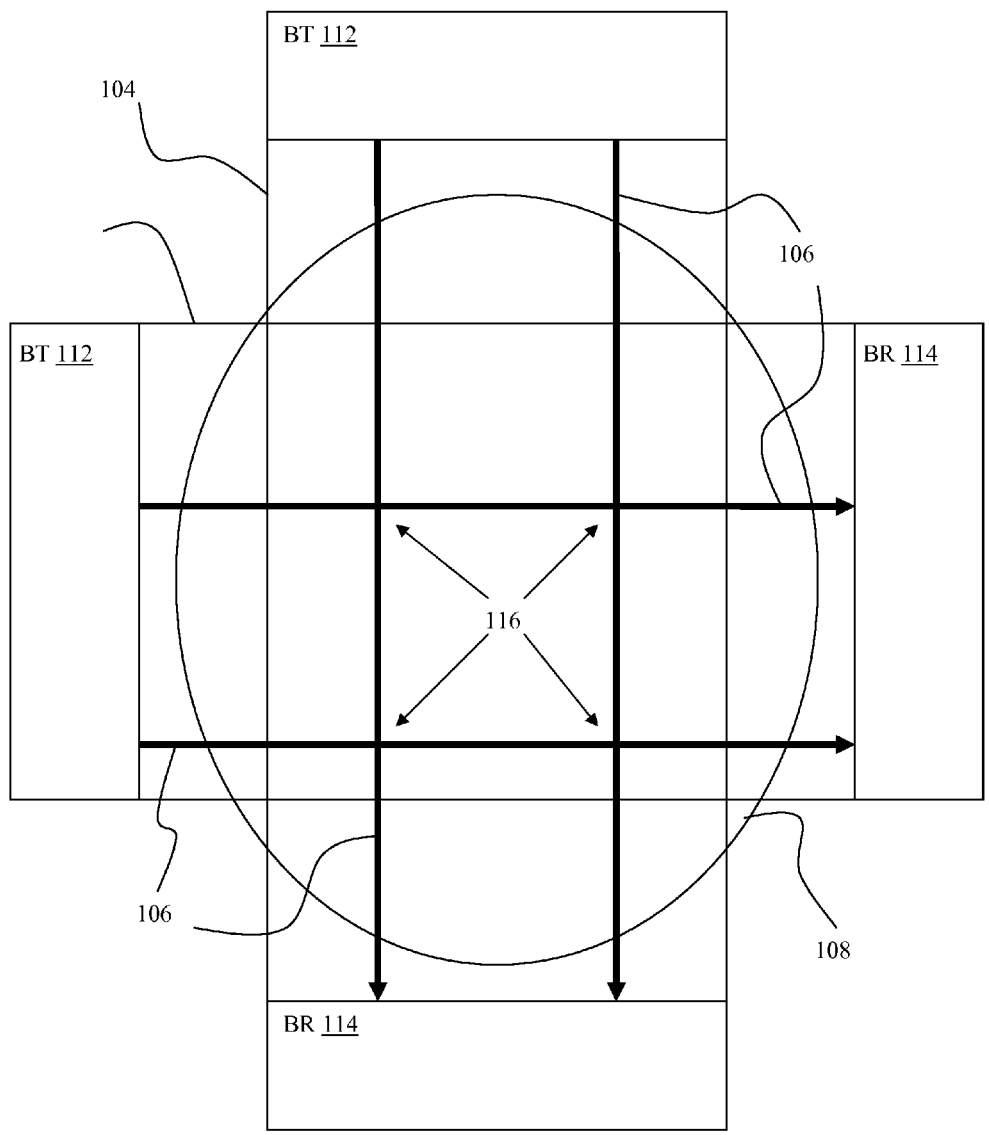
FIG. 2 shows a schematic diagram of one embodiment of the invention.

FIG. 2 shows an enlarged schematic diagram of a part of gas mixture measuring device 100 including a plurality of laser devices 104. In this case, the plurality of laser devices 104 may be deployed as an array. A plurality of beams 106 extends through in-situ non-restrictive flow path of gas mixture 108. (In-situ non-restrictive flow path of gas mixture 108 is illustrated here as a circle but a cross-section of flow path of gas mixture 108 is not restricted to a particular shape.) Each of the plurality of laser devices 104 may obtain a temporally simultaneous dynamic measurement of the at least one species in gas mixture 108. At least two laser devices 104 may be oriented so that at least two beams 106 intersect. The location of a beam intersection 116 may be obtained. FIG. 2 shows four laser devices 104, four beams 106, and four beam intersections 116. However, a person skilled in the art will readily recognize that four is merely illustrative and that any number of laser devices 104, beams 106 and beam intersections 116 may be employed. A plurality of beam intersections 116 provides a grid of dynamic measurements over a cross-section of in-situ non-restrictive flow path of gas mixture 108. In one embodiment of the invention at least one of the plurality of laser devices 104 is calibrated to obtain dynamic measurements of a different species than the at least one species in gas mixture 108.

Referring again to FIG. 1 gas mixture measurement device 100 may include at least one transmission device (TD) 120 for transmitting the obtained dynamic measurements to a receiver (R) 122. Receiver 122 receives dynamic measurements and may submit dynamic measurements for analysis.

Transmission device 120 and receiver 122 may include any known or later developed transmission device 120 and receiver 122 such as electrical and optical wires, or any known or later developed radio-frequency identification tag (RFID). RFID may provide further opportunities for placement of the gas mixture measurement device 100 without the restriction of wires. Transmission device 120 and receiver 122 may allow for analysis of the dynamic measurements in a location other than the location of the gas mixture 108.

Gas mixture measurement device 100 may include gas mixture measurement analysis system 118. Gas mixture measurement analysis system 118 may include a concentration comparison system 123, a concentration trend calculator 124 and a concentration trend comparison system 125. Dynamic measurements may be stored in a dynamic measurements database (DMD) 128.

Concentration comparison system 123 may compare a concentration with a reference concentration. The reference concentration may be a single value, multiple values, or a range of values. The reference concentration may be stored in a reference concentration database (RCD) 131. The concentration may match or deviate from the reference concentration. Concentration matches or deviations from the reference concentration may indicate conditions in gas mixture 108 or source of gas mixture 102. For example, the existence or absence of explosive or hazardous conditions in gas mixture 108 may be indicated. Further, concentration matches or deviations from reference concentrations may indicate whether a source of gas mixture 102 is operating efficiently. In either situation, adjustments or other responses as indicated may be taken.

Concentration trend calculator 124 may calculate a concentration trend for at least one species. For example, concentration trend calculator 124 may use an algorithm to calculate a concentration trend between a current dynamic measurement and a previous dynamic measurement.

An example of an algorithm to calculate a concentration trend between a current dynamic measurement and a previous dynamic measurement includes a slope point formula where m represents the change in concentration of a species over time. A current dynamic measurement may have concentration $c_0$ at time $t_0$ and previous dynamic measurement may have concentration $c_1$ at time $t_1$. The slope may be determined with $m=(c_0-c_1)/(t_0-t_1)$. A person skilled in the art will readily recognize that many known algorithms for calculating concentration trends may be utilized.

Concentration trend comparison system 125 may compare the concentration trend with a reference concentration trend. The reference concentration trend may be a single value, multiple values, or a range of values. The reference concentration trend may be stored in a reference concentration trend database (RCTD) 131. The concentration trend may match or deviate from the reference concentration trend. Concentration trend matches or deviations from the reference concentration trend may indicate conditions in gas mixture 108 or source of gas mixture 102. For example, the existence or absence of explosive or hazardous conditions in gas mixture 108 may be indicated. Further, concentration matches or deviations from reference concentration may indicate whether a source of gas mixture 102 is operating efficiently. In either situation, adjustments or other responses as indicated may be taken.

One advantage of monitoring the rate of change in explosive gas species in gas mixture 108 is a reduction in response time. When concentration trend comparison system 125 indicates a rapid change in the concentration as indicated by a highly positive concentration trend (e.g. a highly positive slope), the response to the presence of a potential explosive gas mixture may be implemented rapidly. Monitoring the rate of change of concentration of a species in gas mixture 108 allows remedies to be implemented that are commensurate to the implied risk.

Figure 3:
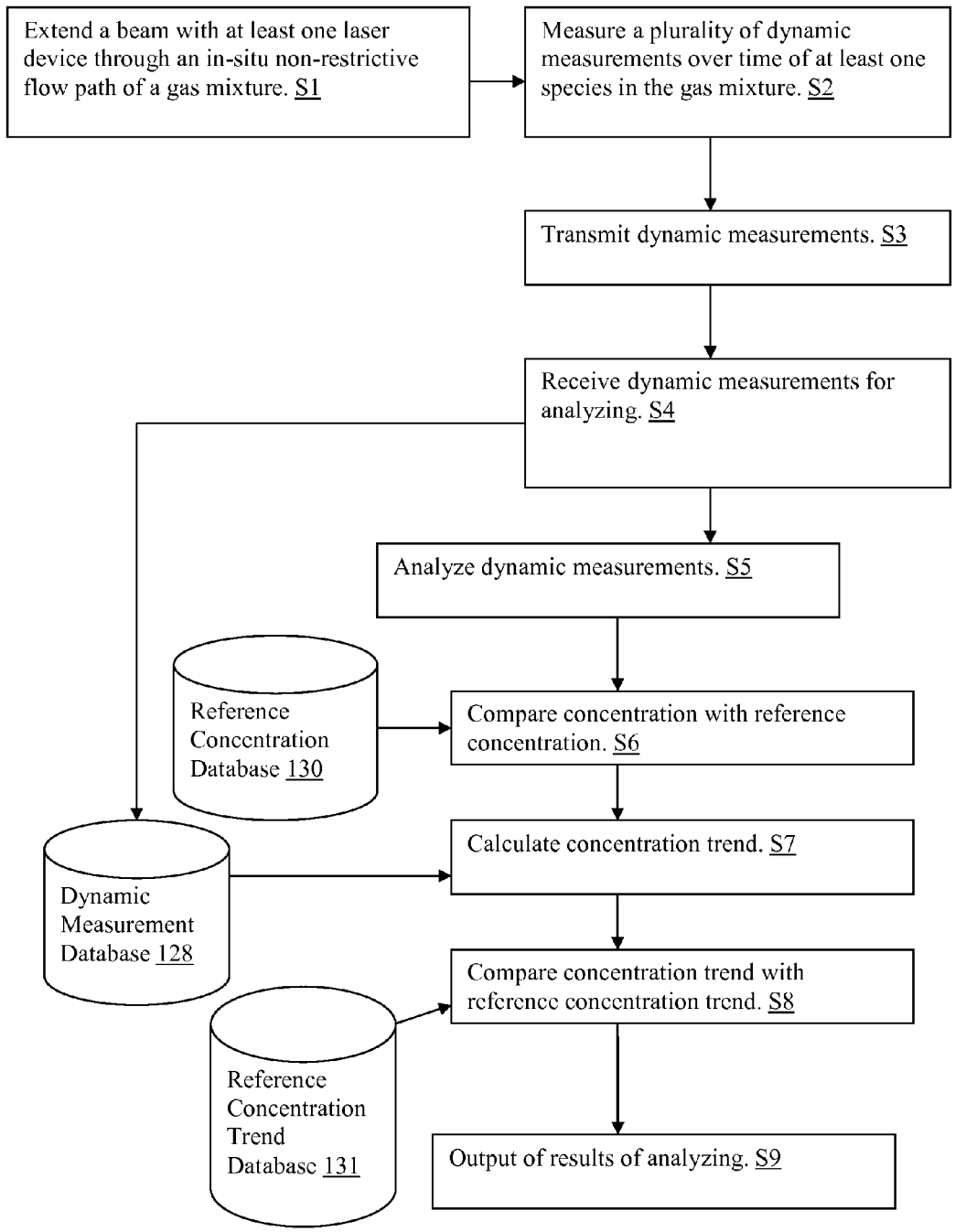
FIG. 3 shows a flow diagram of one embodiment of the invention.

Referring to FIG. 3, a flow diagram of method of gas mixture measurement in one embodiment of the invention is shown. Method starts with extending a beam with at least one laser device 104 through an in-situ non-restrictive flow path of a gas mixture 108 S1. Measurer 110 may measure a plurality of dynamic measurements over time for at least one species in the gas mixture 108 S2. Transmission device 120 may transmit the dynamic measurements S3 to a receiver 122. Receiver 122 receives dynamic measurements for analyzing S4. Gas measurement analysis system 118 may analyze the dynamic measurements S5. Analyzing may include concentration comparison system 123 comparing a concentration for a least one species from the dynamic measurements with a reference concentration S6. Analyzing may include concentration trend calculator 124 calculating a trend of concentration for at least one species S7. Analyzing may include concentration trend comparison system 125 comparing a concentration trend for at least one species with a reference concentration trend S8. Results of analyzing S5 may then be output using any known or later developed method or device for communication.

In FIG. 1, computer system 130 is shown in communication with gas mixture measurement device 100 described herein. Further, computer system 130 is shown in communication with a user 132. User 132 may, for example, be a programmer or operator. User 132 may also be a device or a computer. Interactions between these components and computer system 130 will be discussed in subsequent portions of this application. Computer system 130 is shown including a processing component (PC) 134 (e.g., one or more processors), a storage component 136 (e.g., a storage hierarchy), an input/output (I/O) component 138 (e.g., one or more I/O interfaces and/or devices), and a communications pathway 140. In one embodiment, processing component 134 executes program code, such as gas mixture measurement analysis system 118, which is at least partially embodied in storage component 136. While executing program code, processing component 134 can process data, which can result in reading and/or writing the data to/from storage component 136 and/or I/O component 138 for further processing. Pathway 140 provides a communications link between each of the components in computer system 130. I/O component 138 can comprise one or more human I/O devices or storage devices, which enable user 132 to interact with computer system 130 and/or one or more communications devices to enable user 132 to communicate with computer system 130 using any type of communications link. To this extent, gas mixture measurement analysis system 118 can manage a set of interfaces (e.g., graphical user interface(s), application program interface, and/or the like) that enable human and/or system interaction with gas mixture measurement analysis system 118.

In any event, computer system 130 can comprise one or more general purpose computing articles of manufacture (e.g., computing devices) capable of executing program code installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, gas mixture measurement analysis system 118 can be embodied as any combination of system software and/or application software. In any event, the technical effect of computer system 130 is to provide processing instructions for gas mixture measurements.

Further, gas mixture measurement analysis system 118 can be implemented using a set of modules 142. In this case, a module 142 can enable computer system 130 to perform a set of tasks used by gas mixture measurement analysis system 118, and can be separately developed and/or implemented apart from other portions of gas mixture measurement analysis system 118. Gas mixture measurement analysis system 118 may include modules 142 which comprise a specific use machine/hardware and/or software. Regardless, it is understood that two or more modules 142, and/or systems may share some/all of their respective hardware and/or software. Further, it is understood that some of the functionality discussed herein may not be implemented or additional functionality may be included as part of computer system 130.

When computer system 130 comprises multiple computing devices, each computing device may have only a portion of gas mixture measurement analysis system 118 embodied thereon (e.g., one or more modules 142). However, it is understood that computer system 130 and gas mixture measurement analysis system 118 are only representative of various possible equivalent computer systems that may perform a process described herein. To this extent, in other embodiments, the functionality provided by computer system 130 and gas mixture measurement analysis system 118 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 130 includes multiple computing devices, the computing devices can communicate over any type of communications link. Further, while performing a process described herein, computer system 130 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As discussed herein, gas mixture measurement analysis system 118 enables computer system 130 to provide processing instructions for gas mixture measurements. Gas mixture measurement analysis system 118 may include logic, which may include the following functions: concentration comparison system 123, concentration trend calculator 124, and concentration trend comparison system 125. In one embodiment, gas mixture measurement analysis system 118 may include logic to perform the above-stated functions. Structurally, the logic may take any of a variety of forms such as a field programmable gate array (FPGA), a microprocessor, a digital signal processor, an application specific integrated circuit (ASIC) or any other specific use machine structure capable of carrying out the functions described herein. Logic may take any of a variety of forms, such as software and/or hardware. However, for illustrative purposes, gas mixture measurement analysis system 118 and logic included therein will be described herein as a specific use machine. As will be understood from the description, while logic is illustrated as including each of the above-stated functions, not all of the functions are necessary according to the teachings of the invention as recited in the appended claims.

While shown and described herein as a gas mixture measurement analysis system 118, it is understood that aspects of the invention further provide various alternative embodiments. For example, in one embodiment, the invention provides a computer program embodied in at least one computer-readable medium, which when executed, enables a computer system to measure gas mixtures. To this extent, the computer-readable medium includes program code, such as gas mixture measurement analysis system 118, which implements some or all of a process described herein. It is understood that the term "computer-readable medium" comprises one or more of any type of tangible medium of expression capable of embodying a copy of the program code (e.g., a physical embodiment). For example, the computer-readable medium can comprise: one or more portable storage articles of manufacture; one or more memory/storage components of a computing device; paper; and/or the like.

In still another embodiment, the invention provides a method of gas mixture measurement. In this case, a computer system, such as computer system 130 (FIG. 1), can be obtained (e.g., created, maintained, made available, etc.) and one or more modules for performing a process described herein can be obtained (e.g., created, purchased, used, modified, etc.) and deployed to the computer system. To this extent, the deployment can comprise one or more of: (1) installing program code on a computing device from a computer-readable medium; (2) adding one or more computing and/or I/O devices to the computer system; and (3) incorporating and/or modifying the computer system to enable it to perform a process described herein.

It is understood that aspects of the invention can be implemented as part of a business method that performs a process described herein on a subscription, advertising, and/or fee basis. That is, a service provider could offer to provide processing instructions for gas mixture measurements as described herein. In this case, the service provider can manage (e.g., create, maintain, support, etc.) a computer system, such as computer system 130 (FIG. 1), that performs a process described herein for one or more customers. In return, the service provider can receive payment from the customer(s)

under a subscription and/or fee agreement, receive payment from the sale of advertising to one or more third parties, and/or the like.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system, comprising:
    at least one laser device extending a beam through an in-situ non-restrictive flow path of the gas mixture;
    a measurer coupled to each laser device for obtaining a plurality of dynamic measurements of at least one species in the gas mixture over time, wherein each dynamic measurement includes a concentration and a time of measurement of the concentration; and
    a gas mixture analysis system, wherein the gas mixture analysis system includes a concentration trend calculator, wherein the concentration trend calculator monitors a rate of change of a concentration of the at least one species in the gas mixture.

2. The system of claim 1, wherein the at least one laser device is one of, a tunable diode laser, a vertical cavity surface emitting laser, and an interband cascade laser.

3. The system of claim 1, wherein each dynamic measurement includes a concentration and a time of measurement.

4. The system of claim 1, further comprising: at least one transmission device for transmitting the obtained dynamic measurements to a receiver.

5. The system of claim 4, wherein the at least one transmission device is a radio-frequency identification tag.

6. The system of claim 4, further comprising: at least one receiver for receiving the dynamic measurements.

7. The system of claim 1, wherein the gas mixture analysis system includes a concentration comparison system.

8. The system of claim 1, wherein the gas mixture analysis system includes a concentration trend comparison system.

9. The system of claim 1, further comprising: a plurality of laser devices.

10. The system of claim 9, wherein each of the plurality of laser devices obtains a simultaneous dynamic measurement of the at least one species in the gas mixture.

11. The system of claim 9, wherein at least one of the plurality of laser devices is calibrated to obtain dynamic measurements of a different species than the at least one species in the gas mixture.

12. The system of claim 1, wherein the at least one laser device is a quantum cascade laser.

13. The system of claim 1, wherein the at least one laser device is placed within the in-situ non-restrictive flow path of the gas mixture.

14. The system of claim 1, wherein the concentration trend comparison system compares the rate of change of the concentration of the at least one species in the gas mixture with a reference rate of change of the concentration of the at least one species in the gas mixture.

15. A method, comprising:
    extending a beam with at least one laser device through an in-situ non-restrictive flow path of a gas mixture;
    measuring a plurality of dynamic measurements of at least one species in the gas mixture over time, wherein each dynamic measurement includes a concentration and a time of measurement of the concentration; and
    monitoring a rate of change of a concentration of the at least one species in the gas mixture.

16. The method of claim 15, wherein the at least one laser device is one of a tunable diode laser, a vertical cavity surface emitting laser, and an interband cascade laser.

17. The method of claim 15, further comprising transmitting the obtained dynamic measurements to a receiver.

18. The method of claim 15, further comprising receiving the dynamic measurements and analyzing the measurements.

19. The method of claim 15, wherein the analyzing includes calculating a trend of concentration of at least one species.

20. The method of claim 15, wherein the at least one laser device is a quantum cascade laser.

* * * * *